US00PP23798P3

(12) United States Plant Patent
Maillard et al.

(10) Patent No.: US PP23,798 P3
(45) Date of Patent: Aug. 6, 2013

(54) SWEET CHERRY TREE NAMED 'RUBILAM'

(50) Latin Name: ***Prunus avium* (L.) L.**
Varietal Denomination: RUBILAM

(75) Inventors: Arsene Maillard, Elne (FR); Laurence Maillard, Elne (FR)

(73) Assignee: Agro Selections Fruits, Elne (FR)

( * ) Notice: Subject to any disclaimer, the term of this patent is extended or adjusted under 35 U.S.C. 154(b) by 364 days.

(21) Appl. No.: 13/064,027

(22) Filed: Mar. 2, 2011

(65) Prior Publication Data

US 2011/0219480 P1 Sep. 8, 2011

(30) Foreign Application Priority Data

Mar. 2, 2010 (QZ) ..... PBR 20100511

(51) Int. Cl.
*A01H 5/00* (2006.01)

(52) U.S. Cl.
USPC ..... Plt./181

(58) Field of Classification Search
USPC ..... Plt./181
See application file for complete search history.

(56) References Cited

U.S. PATENT DOCUMENTS

PP10,578 P * 9/1998 Hurlbut ..... Plt./181

OTHER PUBLICATIONS

UPOV PLUTO Citations for 'RUBILAM'.*

* cited by examiner

*Primary Examiner* — Wendy C Haas
(74) *Attorney, Agent, or Firm* — Westerman, Hattori, Daniels & Adrian, LLP

(57) ABSTRACT

A new and distinct variety of sweet cherry tree. The following features of the tree and its fruit are characterized with the heavy and regular production of large size fruit, with very good flavor and eating quality, with an attractive pink red skin color and with good handling and storage quality.

3 Drawing Sheets

Latin name of the genus and species of the plant claimed: *Prunus avium* (L.) L.

Variety denomination: 'RUBILAM'.

This application claims priority of Community plant variety right No. 2010/0511 filed on Mar. 2, 2010 which is hereby incorporated by reference in its entirety.

BACKGROUND OF THE NEW VARIETY

Field of the Invention

In the field of plant genetics, we conduct an extensive and continuing plant-breeding program including the organization and reproduction of orchard trees, and of which peaches, nectarines, apricots, and cherries are exemplary. It was against this background of our activities that the present variety of sweet cherry tree was originated and asexually reproduced by us in our experimental orchard located near Elne, Pyrénées Orientales, France.

ORIGIN OF THE VARIETY

The present new variety of sweet cherry tree (*Prunus avium* L.) was developed in our experimental orchard located in France. 'RUBILAM' sweet cherry tree originated in a cultivated area of the South of France, in the Pyrénées-Orientales department where it was tested. This zone also called Roussillon is subject to a Mediterranean climate. The winter is generally sweet and the summer is hot and dry. The total amount of cold hours lower than 7° Celsius (C) varies from 600 hours to 1200 hours. The total amount of sunshine hours is an average of 2400 hours to 2800 hours per year.

The 'RUBILAM' variety results from a free pollination of a female parent BIGALISE® ENJIDEL (non-patented). 'RUBILAM' can be pollinated by the variety ROSILAM (patent application filed in 2011). 'BIGALISE® ENJIDEL' (non-patented) is characterized by a good productivity but a slow maturity of fruit. Fruit is of large size, very firm, with a sweet flavor, low acidity, and a shiny red color. The blooming period is late March. The maturity period is early, generally from end of May to beginning of June in the South of France. It has been determined to have unique tree and fruit characteristics making it worthy for commercial fresh fruit production. There are no known effects of this standard rootstock on this scion cultivar. Asexually propagated plants remained true to the original tree and all characteristics of the tree and the fruit were transmitted. The plant was reproduced asexually in Elne, Pyrénées-Orientales department, France.

SUMMARY OF THE NEW VARIETY

The present new and distinct variety 'RUBILAM' of sweet cherry tree produces large fruits with very good flavour, firmness and eating quality. The fruit is further characterized by its attractive bright red color and maturing in the early season in France, near the 25$^{th}$ of May.

BRIEF DESCRIPTION OF THE DRAWINGS

The accompanying photographs show typical specimens of the new variety 'RUBILAM' as depicted in color as nearly true as is reasonably possible in color illustrations of this character. These specimens were obtained near Elne, South of France.

BOTANICAL DESCRIPTION OF THE VARIETY

Figure 1:
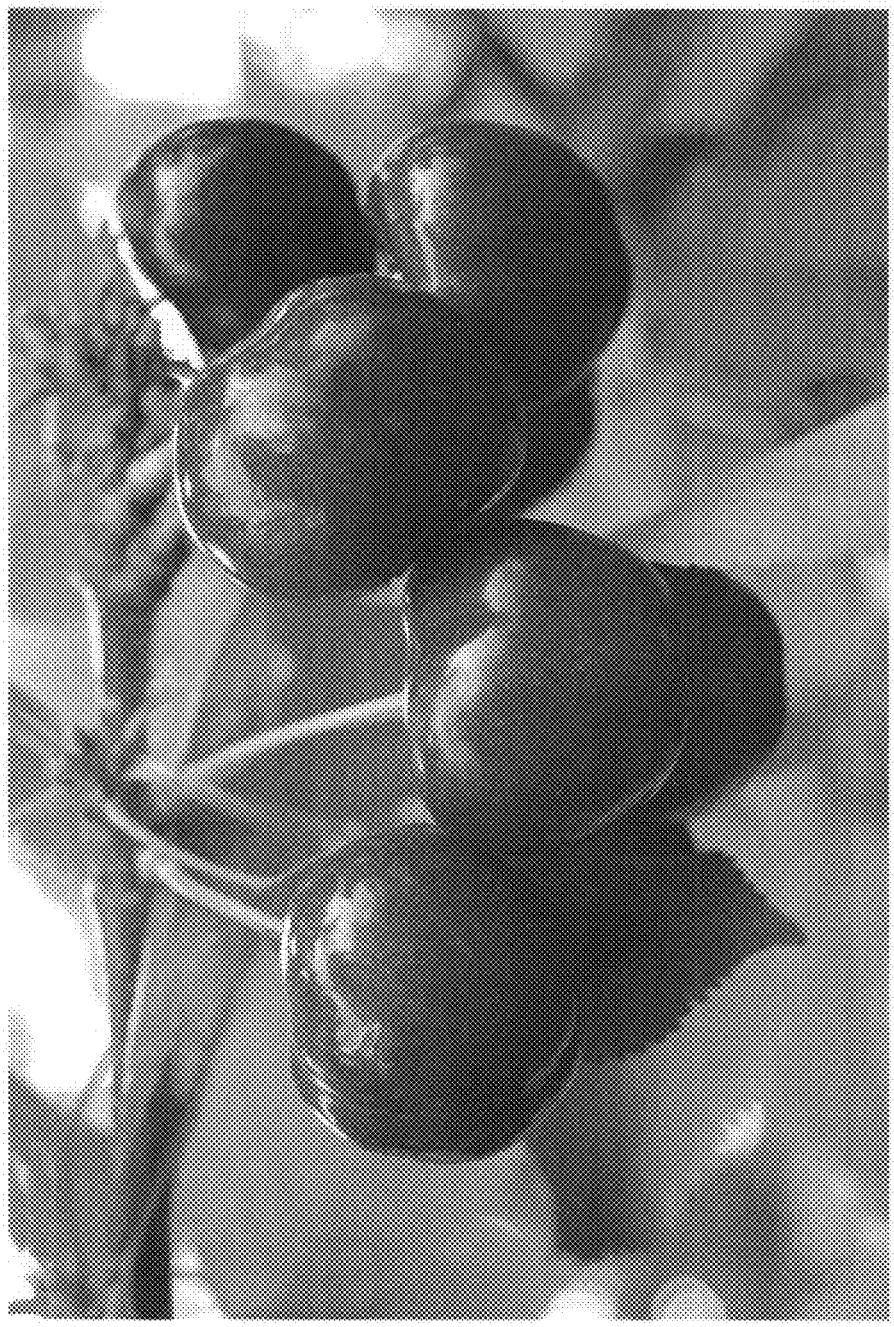
FIG. 1 shows a clustering of typical fruits of 'RUBILAM' variety.
Figure 2:
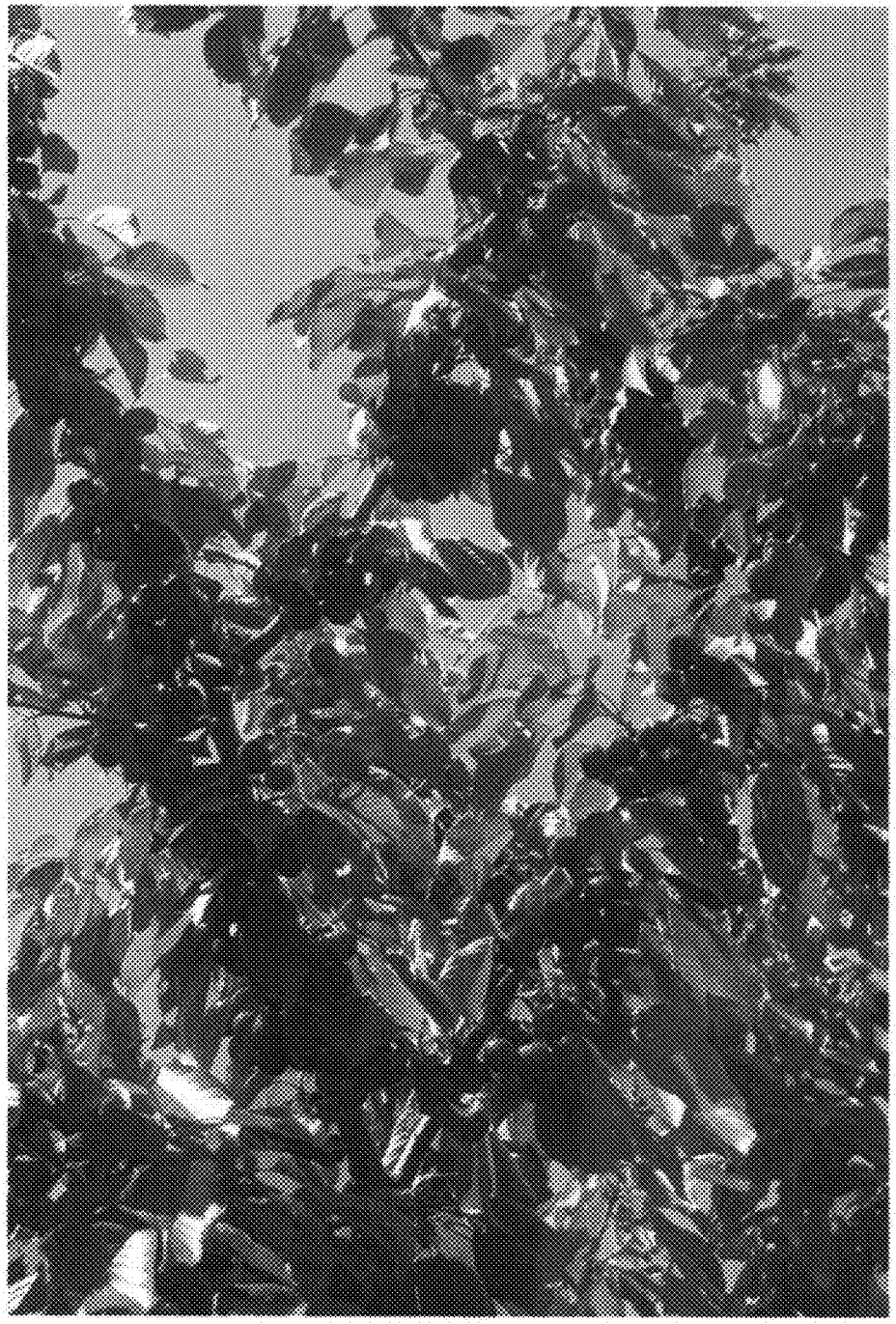
FIG. 2 shows typical 'RUBILAM' branches at maturity, bearing clustering of fruits, and leaves.
Figure 3:
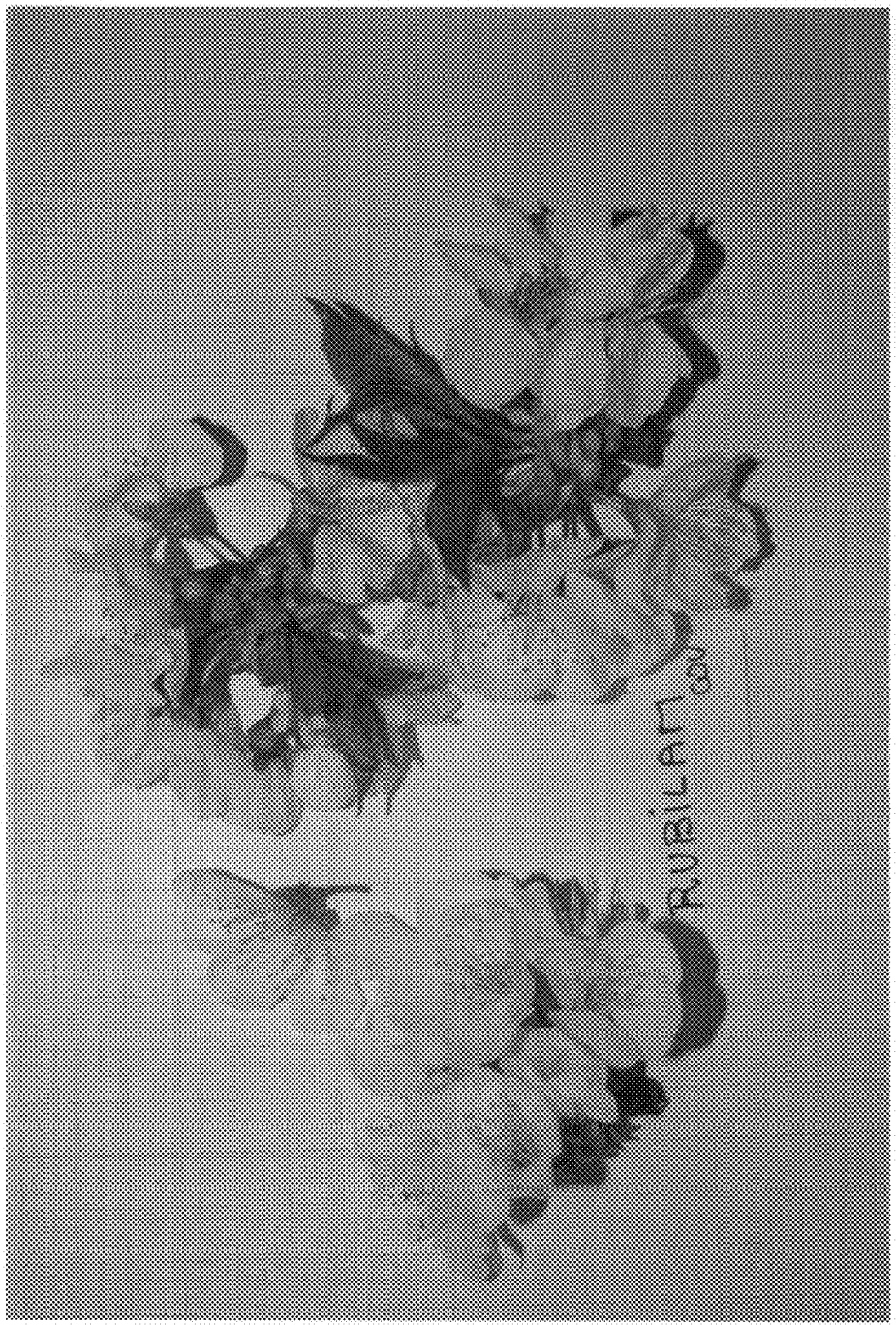
FIG. 3 shows typical white flowers of 'RUBILAM' variety at blooming time.

The following is a detailed botanical description of the new variety of sweet cherry tree, its flowers, foliage and fruit, as based on observations of specimens grown near Elne, South of France, with color in accordance with The R.H.S. Color Chart (Fourth Edition) provided by The Royal Horticultural Society of Great Britain.

The main characteristics of this new variety of sweet cherry are a large fruit size with a bright red color of skin. The fruit flesh is red at complete maturity. The fruit is very firm. 'RUBILAM' is an improvement of the cheery tree variety 'SUMMIT'.

The time of beginning of flowering is semi-early to semi-late and the time of beginning of fruit ripening is also semi-early to semi-late.

In comparison with the reference cherry tree 'SUMMIT', in the South of France climatic conditions, the present variety has different fruit shapes that vary from cordate to round and cordate. The maturity is considered semi-early to semi-late and occurs nears the 25$^{th}$ of May.

Concerning the resistance to pests and diseases RUBILAM is medium sensitive to Monilia.

DETAILED DESCRIPTION

Referring more specifically to the pomological details of this new and distinct variety of sweet cherry tree, the following has been observed under the ecological conditions prevailing at the orchards located near the town of Elne, Pyrénées-Orientales department, France.

All observations have been done on rootstock cultivar. The rootstock was a 'MAXMA 14' tree. The first year the cherry tree is generally cut at 2.80 meters height. The length in one year for each lateral shoot varies from 0.60 m to 0.80 m. We are cutting the cherry trees during the second year to a height of 2.50 meters. The form of the cheery trees is cylindrical and the diameter is limited to 2 m.

All major color code designations are by reference to The R.H.S. Color Chart (Fourth Edition) provided by The Royal Horticultural Society of Great Britain.

Tree:

*Size.*—Medium to high as compared to other commercial sweet cheery cultivars. The tree size the first year was approximately 2.50 meters. The tree was pruned during each following dormant season to a height of approximately 2.50 meters. Current seasons shoots growth could reach 0.80 meters. So the tree size from the second year (second and next years) reached a final height of 3.30 meters with current seasons shoots length comprised.

*Spread.*—Approximately 1.0 meter. The whole orchard was oriented to a central leader organization, with tree lines spaced of 4.0 meters and trees spaced of 1 meter in a same tree line.

*Vigor.*—Medium, tree growth reaching 0.60 to 0.80 meters the first growing season.

*Productivity.*—Good to very good productivity. The new variety produces adequate fruit set annually on a regular basis. The number of the fruit set varies with the prevailing climatic conditions and cultivar practices employed during the bloom period, and is therefore not distinctive of the present variety.

*Bearer.*—Very regular and quantitative. The extinction of the clusters of May improves the calibre and firmness of the fruit.

*Form.*—Naturally spreading to semi-upright.

*Hardiness.*—Hardy in all stone fruit growing areas of south of France and especially where the chilling requirement is between 350 and 1200 hours. No injury with temperatures as low as −12° C. in winter. Good resistance to late frosts.

Trunk:

*Size.*—Measured on 3$^{rd}$ growing season between 4, 5 centimeters and 6.0 centimeters above 30.0 centimeters from ground.

*Bark texture.*—Rather rough with lenticels.

*Lenticels.*—High number of lenticels present on trees from the third growing season. They are 0.2 to 0.3 centimeters in height and 0.4 to 0.8 centimeters in width.

*Lenticels color.*—Lenticels are RHS GREYED GREEN 197 A-C.

*Bark color.*—Grey and silver brown (RHS 166 A to RHS 200 B) with zones RHS GREY 201 C-D.

Branches:

*Size.*—Medium to large for the new growth with average diameter of 5.0 to 9.0 millimeters. Medium to large for the branches at the 3$^{rd}$ growing season.

*Diameter.*—Average diameter of 13.0 to 26.0 millimeters.

*Surface texture.*—Fairly smooth. Wood that is several years old has no furrowed appearance.

*Color.*—Old growth is brown (RHS BROWN 200 B-C) with zones of brown (RHS BROWN 201 B-C).

*Current season shoots.*—Diameter. Average diameter of 5.0 to 9.0 millimeters. Surface texture. Average, wood that is several years old has no furrowed appearance. Crotch angles. Primary branches are considered variable, but the crotch angles are generally between 60 degrees and 70 degrees from the horizontal axis. This particular characteristic is not considered distinctive of the variety, however. Internode. Generally from 30.0 millimeters to 55.0 millimeters length. Color. New growth is more orange brown than the old growth, more or less dark (RHS GREYED ORANGE 176 B-C-D).

Leaves:

*Size.*—Large for the species. Leaf measurements have been taken from vigorous, upright, current-season growth at approximately mid-shoot. The ratio leaf length/leaf width is above 2.10.

*Length.*—From 185.0 to 230.0 millimeters with leaf petiole. Average length with petiole 204.0 millimeters.

*Width.*—From 88.0 to 110.0 millimeters. Average width 97.0 millimeters.

*Leaf base shape.*—Elongated relative to the leaf longitudinal axis.

*Form.*—Elliptic, round base.

*Apex.*—Acuminate.

*Leaf color.*—Color. Upper surface dark green (RHS GREEN 137 A). Lower surface less green (RHS GREEN 137 B-C). The limb lustre is flat. Surface texture. Upper surface generally smooth, glabrous. Lower surface is smooth. Surface venation. Pinnately veined.

*Mid-vein*.—Color. Mid-vein color is light green varying to yellow green (RHS YELLOW GREEN 145 C-D). Margin. Slightly undulating. Margin form. Slightly dentate. Uniformity. Leaves are isolated.

*Leaf petioles*.—Size. Medium to long. Length. Average length 48.0 millimeters. Diameter. Average diameter 2.97 millimeters. Color. Upper surface light red (RHS GREYED PURPLE 183 D to 184 D). Lower surface light green (RHS YELLOW GREEN 145 A-C).

*Leaf glands*.—Size. Average length 2.0 millimeters. Number. Number varies from 3 to 4. Generally 4. Type. Reniform. Color. Light red (RHS GREYED PURPLE GROUP 185 A-B).

*Leaf stipules*.—Generally. No leaf stipules were observed.

Flowers:

*Flower buds*.—Generally. At pre-floral stage of development, the floral buds are conic in form with a round tip. Their form is evolving until blooming, with variables dimensions. Just before blooming, floral buds are approximately 12.0 millimeters wide and approximately 20.0 millimeters long. Color. The base of calyx is generally light green (RHS GREEN 138 A-C to YELLOW GREEN 145 A-B) with pink purple zones (RHS GREYED RED GROUP 182 A-C). The upper part or corolla formed by petals is white (RHS WHITE 155 C). Hardiness. Hardy with respect to South of France climatic conditions. No winter injury was noted during the last several years of evaluation in South of France, with winter temperatures as low as −12° C. in January. The current variety has not been intentionally subjected to drought or heat stress, but the variety showed a very good resistance in orchard to temperatures up to 42° C. with an average temperature between 28° C. and 30° C. during 3 weeks in summer. Date of bloom. Generally late March. The first bloom was observed on Apr. 4, 2003 and the four last blooms took place respectively on Apr. 17, 2007, Mar. 18, 2008, Mar. 25, 2009 and Apr. 6, 2010. Blooming time. Considered semi-early in relative comparison to other commercial sweet cheery cultivars grown in the South of France. The date of full bloom is observed on March. The date of bloom varies slightly with climatic conditions and cultural practices. Blooming period. Average 12 days. This characteristic varies slightly with the prevailing climatic conditions. Type. The variety is considered to have a showy type flower. Size. Considered as large. Flower diameter at full bloom is approximately 34.0 to 40.0 millimeters. Bloom quantity. Considered abundant, approximately at least 60 flowers per meter. Flower bud frequency. Generally 4 to 8 flower buds appear per node.

*Petal*.—Size. Large for the species. Length. Average length 19.0 millimeters. Width. Average width 19.0 millimeters. Form. Broad, elliptic, no overlapping. Count. Nearly always 5. Texture. Smooth and soft. Color. White (RHS WHITE 155 C) on both surfaces. Fragrance. Sweet.

*Petal claw*.—Form. The claw is considered to have a conic form with a rounded tip. Length. Average length 7.0 millimeters. Width. Average length 4.0 millimeters. Margin. Smooth, slightly undulated.

*Petal apex*.—Generally. The petal apices are generally complete at the tip and large round.

*Flower pedicel*.—Length. Medium to large. Length of 10.0 millimeters to 18.0 millimeters. Diameter. Average diameter 1.5 millimeters. Color. Color green (RHS GREEN 144 C-D).

*Calyx*.—Internal surface texture. Smooth and glabrous. Color. The inner surface is yellow washed-green (RHS YELLOW GREEN 145 A-C). The outer surface of the calyx is green (RHS GREEN 138 A-C to YELLOW GREEN 145 A-B) with pink purple zones (GREYED RED GROUP 182 A-C).

*Sepals*.—Texture. Thin. Size. Medium size, elliptic form. Color. Color is green (RHS GREEN 138 A-C to YELLOW GREEN 145 A-B) with pink purple zones (GREYED RED GROUP 182 A-C). Average number of stamens per flower. Average 33 stamens per flower.

*Anthers*.—Length. Medium. Color. Orange yellow red (RHS YELLOW ORANGE 16 A-B) becoming brown after maturity (RHS GREYED ORANGE 175 B-C). Pollen production. Auto-sterile variety. Abundant pollen production. Color is yellow (RHS YELLOW ORANGE 17 B-C) and evolves with maturity.

*Filaments*.—Size. Variable in length, approximately 7.0 to 15.0 millimeters in length. Color. Filament color is white (RHS WHITE 155 C).

*Pistil*.—Number. Generally 1 per flower. Length. Length including ovary 16.0 millimeters to 17.0 millimeters. Texture. Surface glabrous. Color. Color varies from a light green (RHS YELLOW GREEN 150 D) to another light green (RHS YELLOW GREEN 151 D) and evolves with flowering.

Fruit:

*Maturity*.—Very firm at maturity.

*Date of first picking*.—Jun. 7, 2010, varies slightly with climatic conditions. Year 2010 was an exceptionally late season in South of France near Elne.

*Date of last picking*.—Jun. 12, 2010, varies slightly with climatic conditions. Winter 2010 was long and very cold.

*Size*.—Generally. Large. Homogenous. From 1 to 3 fruits per group. Average cheek diameter. Average diameter axially 25.0 millimeters. Average axial diameter. Average transversely in suture plane 28.0 millimeters. Typical weight. Large to very large for the species. Average weight generally superior to 12.0 grams, varies slightly with fertility of the soil and climatic conditions.

*Fruit form*.—Generally. Reniform rounded. Suture. Nearly shallow and smooth, extending from base to apex. No apparent callousing or stitching exists along the suture line.

*Fruit suture*.—Color. The color is generally identical to the entire fruit, i.e. bright red (RED PURPLE GROUP 59 A-B).

*Ventral surface*.—Form. Smooth. Apex. Slight dip, very small, not prominent. Base. Semi-curving, slightly deep. Stem cavity. Average depth is about 4.0 millimeters. Average width is about 12.0 millimeters.

*Fruit skin*.—Thickness. Thin. Texture. Glabrous. Taste. Semi-sweet, very sugared, aromatic. Tendency to crack. None. Color. Homogenous color 100% bright red (RHS RED PURPLE GROUP 59 A-B).

*Fruit stem*.—Size. Medium. Length from 27.0 millimeters to 40.0 millimeters. Average diameter 1.5 millimeters. Color. Light green (RHS YELLOW GREEN 145 A-B). Tenacity. Tenacious to flesh.

*Fruit flesh*.—Ripens. Homogenous. Texture. Very crunchy, luscious, juicy. Fibers. No fibers. Aroma. Pronounced aroma. Eating quality. Very good, very sweet, aromatic. Flavor. Mild flavor, very sweet, aromatic. Slow acidic level. Juicy and aromatic. Juice. Large amount, very juicy. Pink red color (RHS RED GROUP 39 B-C to RED PURPLE 53 A-B). Brix. Superior to 15.0°, varies slightly with amount of fruit per tree and climatic conditions. Color. Red flesh when mature (RHS RED GROUP 53 A-B).

Stone:

*Type*.—Semi-Clingstone.

*Cavity size*.—Small to medium. Rounded and having the same shape as the stone.

*Size*.—Medium.

*Length*.—Average length 11.0 millimeters.

*Width*.—Average width 10.0 millimeters.

*Diameter*.—Average diameter 7.0 millimeters.

*Form*.—Broad, elliptic.

*Base*.—Generally rounded.

*Apex*.—Form. Rounded.

*Stone surface*.—Surface texture. Smooth. Ridges. None, smooth.

*Ventral edge*.—Width. Very low deep.

*Dorsal edge*.—Form. Simple. Color. Stone is yellow (RHS GREYED YELLOW 161 D) when dry. Tendency to split. None.

Kernel:

*Size*.—Small to medium.

*Length*.—Average length 8.0 millimeters.

*Width*.—Average width 6.0 millimeters.

*Thickness*.—Average depth 5.0 millimeters.

*Form*.—Generally oval, little oblique, acute apex, rounded base.

*Pellicle*.—Thin and pubescent.

*Skin color*.—Orange brown (RHS GREYED YELLOW 162 C) with stripes (RHS GREYED ORANGE 164 B).

Use: Dessert. Fresh products. The subject variety 'RUBILAM' is considered to be a sweet cherry tree of the semi-early season of maturity, and which produces fruits that are considered firm, attractively colored. Fruits are excellent for uncooked consumption, crunchy or at full maturity. Due to their flesh quality, firmness and density, they can also be commercialized as $4^{th}$ range product (packed fruit or fruit in bags for example). And they are also useful for both local and very long distance shipping.

Keeping quality: Excellent. Fruit held well for 30 days and more in cold storage at 2° C. and maintained good appearance and eating quality. They have a slow maturation and a long shelf life both on the tree after growth completion and after harvesting without alteration.

Shipping quality: Very good. Fruit showed minimal bruising or scarring during picking, packing and shipping trials. Its resistance to handling during harvest and packing and its long shelf life without alteration after harvest easily permit 4 weeks-shipping at 2° degree Celsius.

Resistance to insects and diseases: Specific tests were run with regards to Monilia and 'RUBILAM' seems low sensitive to Monilia. Moreover 'RUBILAM' is low sensitive to other observed pathologies, to rupture and to conservation pathologies. No sensitivity to *Pseudomonas Syringae* was observed.

Although the new variety of sweet cheery tree possesses the described characteristics when grown under the ecological conditions prevailing near Elne, Pyrénées-Orientales department, France, it should be understood that variations of the usual magnitude and characteristics incident to changes in growing conditions, fertilization, pruning, pest control and horticultural management are to be expected.

We claim:

1. A new and distinct variety of sweet cherry tree, substantially as illustrated and described, characterized by its fruit and especially by its large size, its bright red skin color, its firmness, good flavor and eating quality; the fruit is further characterized by its good handling and storage qualities.

* * * * *